United States Patent [19]

Papenfuhs

[11] 4,369,323

[45] Jan. 18, 1983

[54] PROCESS FOR THE MANUFACTURE OF 2,2'-IMINO-BIS-BENZOTHIAZOLE COMPOUNDS

[75] Inventor: Theodor Papenfuhs, Frankfurt am Main, Fed. Rep. of Germany

[73] Assignee: Hoechst Aktiengesellschaft, Frankfurt, Fed. Rep. of Germany

[21] Appl. No.: 208,189

[22] Filed: Nov. 19, 1980

[30] Foreign Application Priority Data

Nov. 24, 1979 [DE] Fed. Rep. of Germany ....... 2947489

[51] Int. Cl.³ .......................................... C07D 277/82
[52] U.S. Cl. ..................................................... 548/156
[58] Field of Search ................................. 548/156, 161

[56] References Cited

U.S. PATENT DOCUMENTS 3,937,714 2/1976 Barnett ................................. 548/161

FOREIGN PATENT DOCUMENTS 2350875 4/1974 Fed. Rep. of Germany ...... 548/161
602682 7/1978 Switzerland ......................... 548/161

*Primary Examiner*—Donald G. Daus
*Assistant Examiner*—David Springer
*Attorney, Agent, or Firm*—Connolly and Hutz

[57] ABSTRACT

Improved process for the manufacture of 2,2'-imino-bis-benzothiazole compounds in which a 2-amino-benzothiazole compound is heated at a temperature of above 130° C. in the presence of an acidic compound, optionally in a high boiling solvent, or in a high boiling solvent and without an acidic compound, in the latter case especially at a temperature of 200° C. The high boiling solvent may preferably be an acidic solvent. The acidic compound may be used in catalytic amounts up to stoichiometric amounts. Acidic compounds are, for example, hydrochloric acid, sulfuric acid, phosphoric acid or a phenol. The 2,2'-imino-bis-benzothiazoles manufactured according to this process are obtained in pure form and high yield. They can directly be used without further purification for further processing in known secondary reactions. In the new process no difficulty accessible starting products are used, and formation of the toxic methylmercaptan according to known methods is avoided.

8 Claims, No Drawings

PROCESS FOR THE MANUFACTURE OF 2,2'-IMINO-BIS-BENZOTHIAZOLE COMPOUNDS 2,2'-Imino-bis-benzothiazole compounds are known. In the industry, they are used as curing agents (see U.S. Pat. No. 3,726,889) or they are used as starting products for the manufacture of 2,2'-imino-bis-benzothiazoles substituted at the imino nitrogen, such as N,N-bis(2-benzothiazolyl)-sulfenoamides which are also used as curing agents (see U.S. Pat. No. 3,689,467). Moreover, a process for the manufacture of 2,2'-imino-bis-benzothiazoles is known from Journ.Het.Chem. 12 (1), 37–42 (1975) and Synthesis 1971, 504 and 541, according to which S,S-dimethyl-(cyano-imido)-dithiocarbonate is reacted with o-amino-thiophenols. In the technical application, however, this process has several important deficiencies, for example the difficultly accessible starting products and formation of the malodorous and toxic methylmercaptan.

The present invention relates to an improved process for the manufacture of 2,2'-imino-bis-benzothiazole compounds which is easily to be carried out technically and which comprises heating a 2-amino-benzothiazole compound in the presence of an acidic compound at a temperature of above 130° C., for example at a temperature in the range of 130°–210° C., optionally in a high boiling solvent, or in a high boiling solvent and without an acidic compound, in this latter case preferably at a temperature of above 200° C.

The 2-amino-benzothiazoles compound used as starting compound may be reacted under the catalytic effect of an acidic compound as such or in a solvent or diluent expediently boiling above 126° C. When using the acidic compound, the reaction temperature preferably is between 150° and 185° C. The acidic compound, especially a strongly acidic compound such as a mineral acidic compound, may be present in the reaction batch in catalytic amounts, or up to stoichiometric amounts; less acidic, especially organic compounds used as solvents or diluents may even be present in excess. Catalytic amounts are those of less than 0.01 mol, relative to 1 mol of the 2-amino-benzothiazole compound used, preferably 0.001 to 0.01 mol, relative to 1 mol of said starting compound.

The reaction time for the process according to the invention is, in general, between 8 and 20 hours, depending on the starting compound used and the reaction conditions chosen.

Acidic compounds which are used in the reaction and catalyze it are, for example, mineral acids, such as hydrochloric acid, sulfuric acid, phosphoric acid and polyphosphoric acids, including pyrophosphoric acid, moreover acidic high boiling organic compounds which simultaneously may be used as solvents, for example those with phenolic groups, such as phenol, resorcinol, and the different cresols and naphthols, aliphatic and aromatic carboxylic acids, such as propionic acid and benzoic acid. An acidic compound which can be used according to the invention can, however, also be an acidic salt of the 2-aminobenzothiazole compound used as starting compound, which may be added in a catalytic amount to the reaction batch of the 2-aminobenzothiazole compound. Such salts are those of the mineral acids mentioned above, such as the salts of hydrochloric acid, sulfuric acid or phosphoric acid. This strongly acidic salt of a 2-aminobenzothiazole compound can also be used in the reaction as such or in admixture with the corresponding 2-aminobenzothiazole base for the manufacture of the 2,2'-imino-bis-benzothiazole compound according to the invention.

Solvents or diluents in which the reaction can be carried out are high boiling solvents or diluents, preferably with a boiling point above 125° C., which are generally known and which are inert towards the reaction conditions, such as halobenzenes and halotoluenes, halonaphthalenes, tetraline, nitrobenzene, and especially aprotic dipolar solvents, for example dimethyl formamide, N-methyl-pyrrolidone, dimethyl sulfoxide, formamide, N-alkylated acetamides, N-alkylated ureas and N-alkylated phosphoric acid amides such as dimethyl acetamide, tetramethyl urea, tetrabutyl urea and hexamethyl-phosphoric acid amide.

In the reaction according to the invention 2 mols of the aminobenzothiazole compound are reacted while splitting off ammonia which can be bound be the acid. When using catalytic amounts of the acidic compound, the end of the reaction can easily be determined by the end of the formation of ammonia which accompanies the reaction. When stoichiometric amounts of the acidic compound are used, progress and end of the reaction can be observed and determined by analytic supervision, for example by thin-layer chromatography. After the reaction is terminated, the reaction mixture is cooled and optionally diluted with an appropriate solvent wherein the imino-bisbenzothiazole compound is scarcely soluble, or the solvent used in the reaction is removed, for example with steam, and the imino-bisbenzothiazole compound prepared is filtered off, optionally washed with the appropriate solvent and dried. Solvents which are used for precipitating the 2,2'-imino-bis-benzothiazole compounds from the reaction mixture are preferably those miscible in any ratio with the high boiling solvents and diluents used in the process of the invention. This also applies for the solvents with which the compounds obtained according to the invention are rewashed after the isolation. These are, for example, lower aliphatic alcohols and ketones.

The 2,2'-imino-bis-benzothiazole compounds manufactured according to the invention are obtained in pure form and in high yield. They can directly be used without further purification as starting compounds for subsequent reactions.

The method of carrying out the reaction according to the invention in the presence of an acidic compound is preferred. The compounds can be manufactured according to the invention also in the absence of the acidic compound in pure form, but for obtaining an equally good and high yield considerably higher temperatures, in general above 200° C., and longer reaction times are necessary.

The process according to the invention is preferably used for the manufacture of 2,2'-imino-bis-benzothiazole compounds of the formula (1)

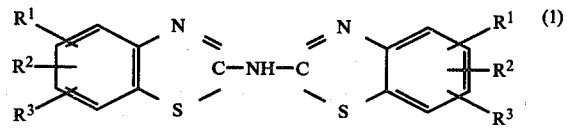

wherein $R^1$ is hydrogen, an alkyl, an alkoxy, a halogen, a nitro group or a cyano group, $R^2$ is hydrogen, an alkyl, an alkoxy, a halogen, or a cyano group and $R^3$ is hydrogen, an alkyl or an alkoxy group, and $R^1$, $R^2$ and $R^3$ may be identical or different from one another. Starting compounds are correspondingly the 2-amino-benzothiazole compounds of the formula (2)

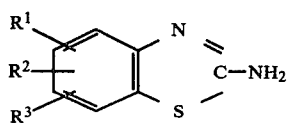

wherein $R^1$, $R^2$ and $R^3$ have the abovementioned meaning.

In the abovementioned substituents $R^1$, $R^2$ and $R^3$ alkyl means an alkyl group, preferably a group of from 1 to 5 C-atoms, especially a methyl and ethyl group, which may be substituted, preferably by an alkoxy group of from 1 to 4 C-atoms; alkoxy means an alkoxy group, preferably a group of from 1 to 5 C-atoms, such as a methoxy and ethoxy group which may be substituted, such as, for example by an alkoxy group of from 1 to 4 C-atoms; a halogen is for example, fluorine and bromine, preferably chlorine.

The process according to the invention is especially preferred for the manufacture of compounds of the formula (1) from the compounds of the formula (2), wherein $R^1$ is hydrogen, methyl, methoxy, ethoxy, β-methoxyethoxy, nitro or chlorine, $R^2$ is hydrogen, methyl, methoxy, ethoxy or chlorine, and $R^3$ is hydrogen or methyl.

The following examples illustrate the invention. Parts are given by weight, percentages are given by weight unless otherwise stated.

EXAMPLE 1

300 Parts of 2-amino-benzothiazole are introduced into 128 parts of molten phenol at a temperature of 50° C. while stirring. The reaction mixture is heated to a temperature of 180° C. and stirred at this temperature for 20 hours. Subsequently the batch is cooled, or 400 parts of ethanol are cautiously added under reflux condensing. Stirring is continued for one hour at about 80° C., the precipitated compound is suction-filtered, washed with ethanol until it is free from phenol and dried.

253 parts of 2,2'-imino-bis-benzothiazole with a melting point of from 257° to 257.5° C. are obtained, corresponding to a yield of 89.4% of the theory. The product is analytically pure and can directly be used as a starting compound for subsequent reactions.

EXAMPLE 1a

The process is carried out as indicated in Example 1, but instead of phenol a corresponding amount of propionic acid or o-cresol or p-cresol is used. The 2,2'-imino-bis-benzothiazolyl-amine is obtained in an equally good yield and quality.

EXAMPLE 2

A mixture of 90 parts of 6-methoxy-2-aminobenzothiazole, 10.8 parts of 6-methoxy-2-aminobenzothiazole chloride and 250 parts of 1,2,4-trichlorobenzene is heated to 160° to 165° C. while stirring; this temperature is maintained for 18 hours while stirring, and subsequently the trichlorobenzene used as solvent is removed by steam distillation The 2,2'-imino-bis-6-methoxy-benzothiazole prepared is suction-filtered from the aqueous suspension thus obtained which is free from trichlorobenzene, and the 2,2'-imino-bis-6-methoxybenzothiazole is dried. It is obtained in a yield of 90.6% of the theory with a melting point of 271° to 272° C. in practically analytically pure form.

EXAMPLE 2a

The process is carried out according to the method indicated in Example 2 but instead of using trichlorobenzene a corresponding amount of 1,2-dichlorobenzene or nitrobenzene is used. The compound manufactured according to the invention is obtained in equally good yield and purity.

EXAMPLE 3

10 Parts of a 96% aqueous sulfuric acid are added dropwise to a solution of 77.6 parts of 6-ethoxy-2-amino-benzothiazole in 100 parts of dimethyl formamide; this reaction mixture is stirred for 16 hours at a temperature of 150° to 160° C. Subsequently, it is diluted with 500 parts of 50% aqueous methanol, the precipitated compound is suction-filtered, washed with water and dried. There are obtained 71.3 parts of a chromatographically pure 2,2'-imino-bis-6-ethoxibenzothiazole with a melting point of 217.5° to 218.5° C. in a yield of 96.1% of the theory.

EXAMPLE 3a

The process is carried out as described in Example 3 but instead of using dimethyl formamide as solvent, the same amount of N-methyl-pyrrolidone or tetrabutyl-urea is used. The same compound as described in Example 3 is obtained in equally good yield and purity.

EXAMPLES 4 TO 21

When carrying out the process according to the invention or as described in the process variants of the above-mentioned Examples 1, 2 or 3 and when using the starting compounds characterized in the Examples of the following Table by the substituents according to formula (2), the 2,2'-imino-bis-benzothiazole compounds according to the formula (1) are obtained with the substituents given in the Examples of the Table in high purity with their characteristic melting points and in the yield mentioned above.

| Ex. | analog. Ex. | $R^1$ | $R^2$ | $R^3$ | Yield % of the theory | Melting point °C. |
|---|---|---|---|---|---|---|
| 4 | 2 | hydrogen | hydrogen | hydrogen | 83.1 | 256–257 |
| 5 | 3 | hydrogen | hydrogen | hydrogen | 91.7 | 257–257.5 |
| 6 | 1 | 4-methyl | hydrogen | hydrogen | 93.7 | 213.5–214.5 |
| 7 | 3 | 4-methyl | hydrogen | hydrogen | 90.0 | 214–214.5 |
| 8 | 3 | 6-methyl | hydrogen | hydrogen | 92.6 | 276–276.5 |
| 9 | 3 | 4-methoxy | hydrogen | hydrogen | 75.2 | 181.5–183 |
| 10 | 3 | 6-methoxy | hydrogen | hydrogen | 96.0 | 271.5–272.5 |
| 11 | 1 | 6-ethoxy | hydrogen | hydrogen | 85.7 | 217–218 |
| 12 | 2 | 6-ethoxy | hydrogen | hydrogen | 81.9 | 216.5–218 |
| 13 | 3 | 4-(β-methoxy)-ethoxy | hydrogen | hydrogen | 82.0 | 102–105 |
| 14 | 3 | 6-nitro | hydrogen | hydrogen | 96.4 | >300 |
| 15 | 3 | 4-chlorine | hydrogen | hydrogen | 91.9 | 270–272.5 |
| 16 | 3 | 4-methyl | 6-methyl | hydrogen | 82.6 | 260–262.5 |
| 17 | 3 | 4-methyl | 7-methyl | hydrogen | 91.8 | 170–172 |
| 18 | 3 | 4-methyl | 6-chlorine | hydrogen | 80.6 | 273–274.5 |
| 19 | 3 | 4-methyl | 7-chlorine | hydrogen | 92.7 | 252–252.5 |

-continued

| Ex. | analog. Ex. | R¹ | R² | R³ | Yield % of the theory | Melting point °C. |
|---|---|---|---|---|---|---|
| 20 | 3 | 4-methoxy | 6-chlorine | 7-methyl | 92.0 | 266.5–267.5 |
| 21 | 3 | 4-methoxy | 7-methoxy | hydrogen | 89.7 | 136–138 |

EXAMPLE 22

A mixture of 75 parts of 2-amino-benzothiazole and 250 parts of 1-chloronaphthalene is heated for 40 hours at 210° C. while stirring. Subsequently, the solvent is removed by steam distillation, and the 2,2′-imino-bis-benzothiazole is filtered off from the aqueous bottom phase. It was washed with water and dried.

Melting point: 256°–258° C.; yield: 46.6% of the theory.

What is claimed is:

1. A process for the manufacture of a 2,2′-imino-bis-benzothiazole compound of the formula

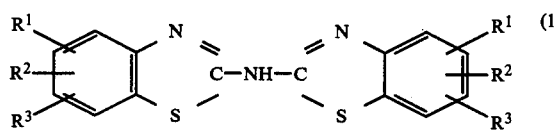 (1)

wherein R¹ is hydrogen, or is alkyl of 1 to 5 C-atoms unsubstituted or substituted by alkoxy of 1 to 4 C-atoms, or is alkoxy of 1 to 5 C-atoms unsubstituted or substituted by alkoxy of 1 to 4 C-atoms, or is halogen, nitro or cyano, R² is hydrogen, alkyl of 1 to 5 C-atoms unsubstituted or substituted by alkoxy of 1 to 4 C-atoms, alkoxy of 1 to 5 C-atoms unsubstituted or substituted by alkoxy of 1 to 4 C-atoms, or is halogen or cyano and R³ is hydrogen, alkyl of 1 to 5 C-atoms unsubstituted or substituted by alkoxy of 1 to 4 C-atoms, or alkoxy of 1 to 5 C-atoms unsubstituted or substituted by alkoxy of 1 to 4 C-atoms, $R^1$, $R^2$ and $R^3$ being identical or different from one another, which consists essentially of heating a 2-amino-benzothiazole compound of the formula

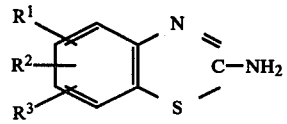 (2)

in which $R^1$, $R^2$ and $R^3$ are defined as above, at a temperature of 130° to 210° C. in the presence of an acidic compound selected from the group consisting of the aliphatic carboxylic acids, hydrochloric acid, sulfuric acid, phosphoric acid, polyphosphoric acid, phenol, the cresols and the hydrochloric, sulfuric and phosphoric salts of said 2-amino-benzothiazole compound.

2. The process of claim 1 wherein said heating is carried out in the presence of a high-boiling solvent or diluent.

3. The process of claim 2 wherein said high-boiling solvent or diluent has a boiling point above 125° C.

4. The process of claim 1 wherein the acidic compound is present in the reaction mixture in a catalytic amount or a stoichiometric amount relative to the 2-amino-benzothiazole compound.

5. The process of claim 1 wherein the acidic compound is hydrochloric acid, sulfuric acid, phosphoric acid or polyphosphoric acid.

6. The process of claim 1 wherein the acidic compound is the hydrochloric, sulfuric or phosphoric salt of said 2-amino-benzothiazole compound.

7. The process of claim 1 wherein the acidic compound is phenol or a cresol.

8. The process of claim 1 wherein said temperature is from 150° to 185° C.

* * * * *